United States Patent [19]

Piasio et al.

[11] 4,098,876

[45] Jul. 4, 1978

[54] REVERSE SANDWICH IMMUNOASSAY

[75] Inventors: Roger N. Piasio, Medfield, Mass.; James W. Ryan, Miami, Fla.; James E. Woiszwillo, Milford, Mass.

[73] Assignee: Corning Glass Works, Corning, N.Y.

[21] Appl. No.: 735,740

[22] Filed: Oct. 26, 1976

[51] Int. Cl.$^2$ .................. G01N 33/16; A61K 43/00
[52] U.S. Cl. ................... 424/1; 23/230 B; 424/12
[58] Field of Search ............. 424/1, 1.5, 12; 23/230 B

[56] References Cited

U.S. PATENT DOCUMENTS

| | | | |
|---|---|---|---|
| 3,850,752 | 11/1974 | Schuurs et al. | 424/12 |
| 3,896,217 | 7/1975 | Johnson | 424/1 |
| 3,975,511 | 8/1976 | Vann et al. | 424/12 |
| 3,995,019 | 11/1976 | Jerome | 23/230 B |

*Primary Examiner*—Benjamin R. Padgett
*Assistant Examiner*—Christine M. Nucker
*Attorney, Agent, or Firm*—William E. Maycock; Clinton S. Janes, Jr.; Clarence R. Patty, Jr.

[57] ABSTRACT

Method of determining the presence and/or concentration of a polyvalent antigenic substance in a fluid. The method comprises the steps of incubating the fluid with labeled antibodies to the substance to form a first labeled immunochemical complex and then incubating that complex with immobilized antibodies to the substance to form a second labeled complex which is separated from the incubation medium. The amount of label in the second complex provides a means for detecting and/or quantitating the substance in the fluid. By reversing the sequence of incubation steps in a "two-site" or sandwich assay, greater sensitivity is achieved and an intermediate washing step is eliminated.

31 Claims, 1 Drawing Figure

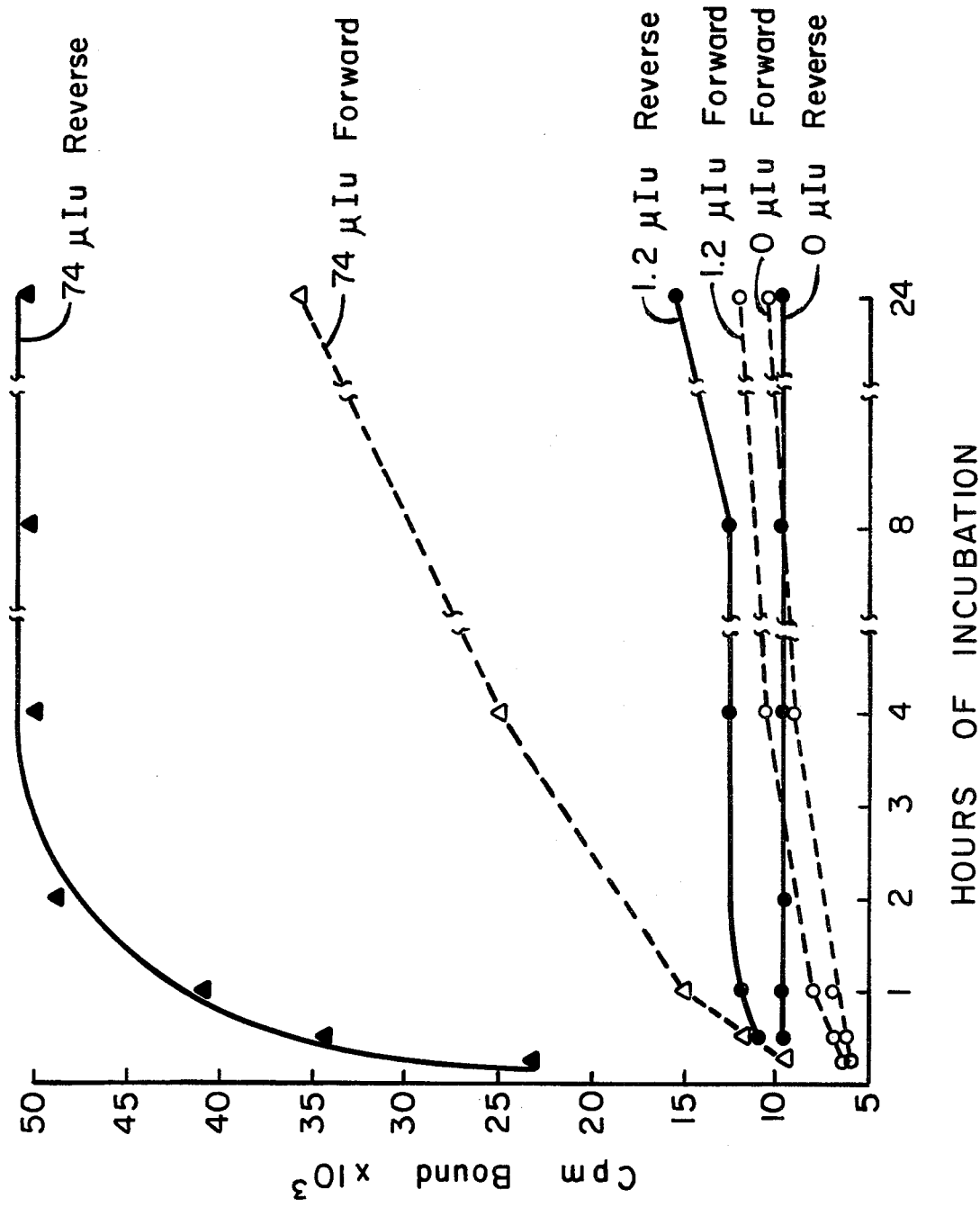

REVERSE SANDWICH IMMUNOASSAY

BACKGROUND OF THE INVENTION

1. Field

This disclosure is concerned generally with methods of detecting and/or determining the concentration of various substances found in fluids, especially human body fluids. More specifically, the disclosure is concerned with a method of determining such substances via solid phase immunoassay techniques.

2. Prior Art

The expression immunoassay, as used herein, refers to a method of determining the presence or concentration of a subtance in a fluid which method is based on the use of antibodies specific to that substance. Since it is known that antibodies to a given substance are extremely specific to that substance, research efforts have been directed in recent years to use that specificity in determining the presence or concentration of substances which are present in very small quantities in fluids, especially human body fluids such as blood. Although there now exists a wide variety of immunoassay techniques, the more common assays require the use of a label for either the antibody or the antigenic substance or hapten being determined. The use of a label permits a relatively rapid detection or quantitation in conventional laboratories using conventional equipment. A variety of labels are known and used in immunoassays. For example, fluorogenic materials useful in a fluoroimmunoassay (FIA) are described in U.S. Pat. No. 3,940,475, to Gross. Enzyme markers can be coupled to antibodies or antigens to perform an enzyme immunoassay (EIA) as illustrated in U.S. Pat. No. 3,654,090, to Schuurs et al. Radioisotopes can be incorporated into an antibody or substance to perform a radioimmunoassay (RIA) as illustrated in U.S. Pat. No. 3,555,153 to Axen et al. As used herein, the expression labeled antibody or its equivalent, includes any of those known labels.

A typical immunoassay requires, at some point, an immunochemical complexation between an antigenic substance and its respective antibody. Commonly, one of the species in such a complexation is labeled, and, by competing with, complexing with, or displacing an unknown substance in such complexation, and then quantitating the label (e.g. fluorometrically, enzymatically, radiometrically, etc.), it is possible to determine the unknown by known means. Prior to such quantitation, however, it is generally necessary to separate the immunochemically complexed products from the surrounding incubation medium. Such separations can be facilitated by providing one of species involved in an immobilized, insoluble, form. For example, it is known that antigenic substances, haptens, or antibodies thereto can be attached to, or incorporated in, various water insloluble carrier materials without substantial loss of biological activity. See for example, U.S. Pat. Nos. 3,555,153 (organic carriers) and 3,652,761 (inorganic carriers). When either of the reactants in an immunoassay is used in such an immobilized form, there is present a solid phase which, when appropriate, can be readily separated (e.g. by centrifugation) for label quantitation. The use of composites comprising antibodies or antigens associated with or immobilized on essentially water insoluble carrier materials is commonly referred to as a solid phase immunoassay (SPIA). As used herein, the expression immobilized antibody composite or the equivalent includes all forms of antibodies which have been attached to insoluble materials.

A wide variety of solid phase immunoassays have been developed in response to analytical needs and limitations. A number of these assays have been described in detail in *Radioimmunoassay Methods*, Ed. K. E. Kerkham & W. M. Hunter, Churchill Livingston, Edinburgh & London (1971). See specifically the chapter by L. Wide, "Solid Phase Antigen-Antibody Systems", pp. 405–413. In the above reference, there is described a so-called "sandwich" technique for the assay of antigens. See System 3 at p. 408. That system is based on the use of solid phase coupled antibodies and antibodies which have been labeled with a radioisotope. The antigen being assayed is initially complexed with the immobilized antibody by simply incubating the immobilized antibody composite with a fluid sample containing the antigen. The incubation period is about 24 hours. After the incubation period, the solid phase product is washed and then reacted with labeled antibodies which complex with the antigen already complexed on the solid phase antibodies. The uptake of labeled antibody (which can be conveniently counted) is directly correlated to the amount of antigen in the test solution. As noted in the above publication, the system is based on the use (and existence) of an antigen which can be bound to at least two antibodies simultaneously. Such antigens are referred to herein as polyvalent antigens and a variety of such antigens are known (e.g. hepatitis associated antigen or HAA, throid stimulating hormone or TSH, carcinoembryonic antigen or CEA, etc.).

Another system described in the above publication is the "Radiometric" assay (see System 6, p. 411). That assay, referred to as an immunoradiometric assay, involves incubating labeled antibodies with serum to be tested to complex antigens in the serum. After an incubation period, a solid phase coupled antigen is added to bind the remaining "free" antibodies. The radioactivity in the liquid phase is directly correlated with the amount of antigen in the sample. For maximum efficiency in this system, the antigens should have only one site capable of complexing with an antibody. Such antigens can be and are referred to herein as monovalent.

The present disclosure is based on our discovery that the certain features of known sandwich immunoassays such as that disclosed in System 3 of the cited publication (or recently issued U.S. Pat. No. 3,867,517 to Ling) and our own observations result in a novel sandwich immunoassay, the methodology of that assay being the reverse of that presently employed. By reversing the steps of known solid phase sandwich assays, we have found that a higher degree of sensitivity is possible and additionally tedius and time consuming intermediate wash step is eliminated. Details of our method are described hereunder.

BRIEF DESCRIPTION OF THE FIGURE

The FIGURE is a graph which compares sensitivities for TSH radioimmunoassays in the known forward method with the reverse method disclosed herein.

SUMMARY OF THE INVENTION

Our method for determining the presence or concentration of a polyvalent antigenic substance (or hapten) in a fluid comprises the steps of: (a) incubating the fluid with labeled antibodies to the substance under conditions sufficient to form a first labeled immunochemical complex; (b) incubating the first labeled complex with a composite comprising antibodies to the substance immobilized on a water insoluble carrier material, the incubation being under conditions sufficient to form a second labeled complex comprising the first complex complexed to the composite; (c) separating the second complex from the incubation medium; (d) determining the amount of label associated with the second complex, and (e) relating the determination of step (d) to a standard to ascertain the presence or concentration of the substance in the fluid. Various preferred embodiments of our method are described below.

SPECIFIC EMBODIMENTS

Our method comprises five basic steps: (1) a first incubation with the sample fluid and the labeled antibody; (2) a second incubation with the immobilized antibody; (3) a separation step; (4) a label quantitation step; and (5) a correlation setp. As indicated above, our assay differs from known sandwich assays not only on the basis of the order of steps used but on the mechanisms involved. For example, certain known solid phase sandwich immunoassays involve (1) incubating a sample fluid with an immobilized antibody; (2) incubation with a labeled antibody; and then steps (3) – (5) above. The known system can be deemed a "forward" solid phase sandwich assay. Our system reverses the first two steps and can be referred to herein as a "reverse" solid phase sandwich immunoassay. By reversing the sequence of the first two steps, we have been able to achieve a higher assay sensitivity and, where the assay is used for concentration determinations (c.f. mere detection as in HAA assays), an intermediate washing step is eliminated. In the examples below, we describe how our method can be used to detect or quantitate three polyvalent (having at least two antibody complexing sites) antigenic substances. Illustrative examples are given for performing reverse solid phase sandwich immunoassays for (1) detecting the presence of hepatitis associated antigen (HAA) in a blood serum sample; (2) determining the concentration of thyroid stimulating hormone (TSH) in a serum sample; and (3) determining the concentration of carcinoembryonic antigen (CEA) in a sample. Prior to the illustrative examples, various methods of accomplishing the five basic steps of our method are disclosed.

(1) The first incubation: The sample fluid for this step may be any liquid containing, or suspected of containing, the polyvalent antigen to be determined or asayed. As a practical matter, it is anticipated that the more common sample fluids will be human body fluids such as blood serum, urine, etc., although it should be appreciated that our method can also be used for verifying the accuracy of standards and for other non-body fluid uses. The labeled antibodies of this step must be highly specific to, and capable of tightly complexing with, the substance being assayed. The unlabeled antibodies can be obtained by known means by injecting the antigenic substances (or, in the case of very small substances, a conjugate thereof) in a host animal capable of immunochemical response to the injection. The appropriate antibodies (antiserum) are then purified and labeled by known means (e.g. with enzymatic, fluorogenic, radiometric, etc. labels or markers). After the antiserum is labeled, a quantity is incubated with the ample to be assayed under conditions sufficient to assure complexation of the antigenic substance being assayed. In the case of a "yes/no" type assay (e.g. HAA) the amount of labeled antiserum need only be enough to complex with a detectable amount of the antigen (e.g. enough antiserum so that a positive sample can be readily and reliably distinguished from a known negative using the same label). For assays to determine the concentration of a given substance, enough labeled antiserum should be added to assure complexation (but not "sandwiching") of substantially all of the substance which might be present. The actual minimum and preferred maximum amounts can be determined experimentally and/or be based on knowing such factors as the clinically significant concentration range of the substance, antiserum concentration, titer, etc.

As a practical matter, we have found that the amount of labeled antibody (Ab*) added to the sample for the first incubation should be sufficient to give a statistically significant signal to noise response for an antigen concentration in the clinically significant range (average) or for the least detectable concentration of interest. Additionally, it can be shown both experimentally and mathematically that the range of our assay system can be controlled by varying the quantity and specific activity of the labeled antibody. As a practical matter, this control of antigen detectability can not be readily achieved using the standard forward method (which uses an excess of Ab* and IMAB) because an "open faced sandwich" is not used as in the case of our reverse method.

As a general rule, using our methods, the first incubation can be accomplished in about two hours or less at room temperature or slightly elevated temperatures (e.g. about 18° to 50° C.). This is a clear advantage over past incubation periods for some other sandwich assays. Although ideal incubation conditions may vary from assay to assay, a preferred incubation is from 10 to 120 min. at 18° to 50° C. The first incubation can be illustrated as AB* + AG → AB*.Ag where Ab* represents the labeled antibody and Ag represents the antigen or substance being assayed.

(2) The second incubation: Unlike standard "forward" sandwich assays which ideally require two separate intermediate washes to remove uncomplexed antigen, our reverse system requires no washes at all. This is a decided advantage in simplifying the assay and minimizing chances for errors. Hence, the second incubation can follow the first by merely adding the appropriate immobilized antibodies to the incubation medium. The second incubation, preferably for 5 to 30 minutes at 18° to 50° C. should be under conditions sufficient to assure complexation of substantially all complexed products of the first incubation if the substance is being assayed for concentration to maximize signal to noise response. For the yes/no type assay, the second incubation must be under conditions sufficient to assure complexation of enough labeled first complex to permit reliable detection against a negative control sample. Preferably, the antibodies are immobilized on a water insoluble, inert carrier material in a manner which yields a composite capable of relatively quick, unrestricted interaction with the first complex solution. This interaction can be assured by using antibodies fixed on the surfaces of many different carriers known to those skilled in the art. For illustrative purposes only in our examples, we used high surface area (i.e. $> 5$ m$^2$/g) glass particles as carriers. The particles had an average size of about .8 to 2.0 microns and were surface activated by silanization for coupling the antibodies thereto by known means (see, for example, U.S. Pat. No. 3,652,761 to Weetall or U.S. Pat. No. 3,975,511 to Vann et al.). The second incubation can be illustrated as AB*-

.AG + IMAB → AB*.Ag.IMAB, where IMAB represents the immobilized antibody.

(3) The separation step: To accurately read the results of the second incubation, and, hence, complete the assay, the labeled solid phase reaction products (AB*.Ag-.IMAB) must be separated from the incubation medium which may contain free label in excess of that required to complex with the antigen. Since the reaction products constitute a solid phase which is water-insoluble because of the carrier, separation can be accomplished by conventional means such as sedimentation or centrifugation. It can be appreciated that other separation means are available (e.g. such as the use of magnetism on magnetically responsive carriers as disclosed in U.S. Pat. No. 3,933,997). As a practical matter, however, a simple centrifugation step is preferred and in the examples below, unless otherwise indicated, all separations of solid phase materials were accomplished by centrifugation in a common centrifugation tube at about 500 to 1500 RCF for 2 to 10 minutes.

(4) Label Quantitation Step: Since the detectability or quantitation of the substance being assayed is directly related to the amount of labeled antibody associated with the solid phase complex (AB* Ag.IMAB), it is clear that the label (and hence, the substance) can be quantitated by at least two methods - i.e. a direct quantitation of the solid phase complex or indirectly by quantitating the non-solid phase label in solution and then simply subtracting that amount from the total label offered. As a practical matter, however, it is convenient to simply directly quantitate the label in the solid phase incubation reaction products. The ideal quantitation technique depends to some extent on the label used in the system. For example, where the label is a fluorogenic material, the material should be in the form acceptable to common fluorimeters. Where the label is an enxyme which is conjugated to the antibody by known means (e.g. U.S. Pat. No. 3,654,090), the quantitation system should be capable of enzymatic analysis. Where radioisotopes are used as labels for the antobidies, the quantitation radioactivity counting equipment. In the examples below we used $I^{125}$ labeled antibodies as labels although the principles disclosed herein are applicable to any sandwich immunoassay system, regardless of label used.

(5) The Correlation Step: After the label quantitation step, the results may be related to the substance concentration or presence determination by known means. For exaple, where the substance concentration is being determined (e.g. TSH) the label quantitation can be related to a standard curve prepared using known amounts of the substance. In the case of yes/no type assays (e.g. HAA), the label quantitation may be correlated with a negative control and/or a minimum label quantitation number needed to establish a true positive. It can be appreciated that various means of correlating the label count results of the separation step in an immunoassay are well known. In our examples, the concentration of TSH was determined using a standard curve. In the yes/no assays for HAA, a "sample" was deemed positive, if, with it, the label quantitation step showed a label at least 2.1 times as great as a control (when $I^{125}$ is the label for the respective antibody). As used herein, the expression standard, when used with reference to the label quantitation step, includes the above and other correlation means.

Our method is disclosed in further detail in the illustrative examples below.

EXAMPLE I (TSH Assay)

Assays for thyroid stimulating hormone (TSH) were performed in both the "forward" mode and the "reverse" mode of this disclosure ring $I^{125}$ labeled anti-TSH antiserum as the labeled species. The antiserum was obtained from rabbit.

The antiserum was labeled with the tracer according to the method of Hunter and Greenwood.

The immobilized anti-TSH composite consisted of the antiserum chemically coupled to the surfaces of silanized glass particles via a diazo linkage. The particles had an average particle size ranging from about 0.8 to 2.0 microns.

Samples containing 0, 1.2, and 74 μIU amounts of TSH were assayed by otherwise standard RIA techniques in both the forward and reverse modes.

A commonly accepted normal range for TSH concentration is about 2 to 10 μIU.

In the conventional forward RIA method, all sample concentrations (200 λ or 200 lambda sample size) were incubated with an excess (~2 mg) of the immobilized antibody (IMAB) at 37° C. to complex substantially all TSH with the IMAB (first incubation). Then, after one wash, the solid phase complex was incubated with 240,000 cpm of the labeled antibody (about 0.500 ml) for one hour at 37° C.

In the reverse assay method of this disclosure, the 200 λ samples were incubated initially with the labeled antiserum (240,000 cpm, about 0.500 ml), for one hour at 37° C. Then, without a washing step, a larger amount of IMA (~10 mg) was incubated with the sample for ½ hour at 37° C.

In the "reverse" mode normally two to five times the amount of immobilized antibody is used with respect to the amount used in the forward mode. This is necessary because in the reverse mode the immobilized antibody must bind not only the immune complexes, but also any unbound antigen in order to yield maximum sensitivity. This is demonstrated in example II (HAA).

The final labeled products were separated by centrifugation at 1000 RCF for 5 minutes and counted using an autogamma scintillation spectrometer. The results are compared in the table below.

TABLE I

| | Counts per minute vs. TSH Concentration/ml | | | |
|---|---|---|---|---|
| | 1st Incubation Time (hr) | 0 μIU | 1.2 μIU | 74 μIU |
| Forward Method | | | | |
| Total Counts* 240,000 cpm | .25 | 6034, 6044 | 6250, 6501 | 8615, 9289 |
| | .50 | 6540, 6708 | 6624, 6713 | 11086, 11095 |
| | 1 | 7176, 7373 | 7952, 7301 | 15012, 14726 |
| | 4 | 9047, 9498 | 9847, 10716 | 24722, 25131 |
| | 22 | 11329, 11608 | 12014, 11801 | 36133, 35661 |
| Reverse Method | | | | |
| | .25 | 9317, 9807 | 10830, 10269 | 29567, 29020 |

TABLE I-continued

| Counts per minute vs. TSH Concentration/ml | | | |
|---|---|---|---|
| 1st Incubation Time (hr) | 0 μIU | 1.2 μIU | 74 μIU |
| .50 | 9452, 10093 | 10830, 11270 | 34692, 34467 |
| 1 | 9086, 9746 | 11536, 11383 | 41346, 41012 |
| 4 | 9723, 10470 | 12861, 12423 | 42789, 43448 |
| 22 | 9667, 9658 | 16195, 16599 | 50538, 52410 |

*Tag purity approximately 25%

As can be seen from the above results, the presently disclosed method provides a greater assay sensitivity. This is illustrated by the graph of the figure where standard curves covering the clinically significant ranges of TSH are compared in both the forward and reverse mode.

EXAMPLE II (HAA Assay)

An assay for hepatitis associated antigen in a blood serum sample is basically a yes/no type test. When the test is done via RIA techniques, there is typically a known negative control. Generally, if the sample being assayed is found to be 2.1 times as labeled (e.g. radioactive) as the control, the sample is deemed positive. Thus, to avoid borderline results which might have to be repeated, it is desirable to have a highly sensitive test. As in the TSH assay, a higher degree of sensitivity (that is, signal to noise response) was observed by testing for HAA in the reverse mode.

For the reverse assay, a 200 λ standard positive HAA sample was subjected to a first incubation with 2 count levels of $I^{125}$ labeled anti-HAA antiserum for ½ hour at 45° C. Then, the resulting complex was incubated with 2 levels of immobilized anti-HAA antibodies for one half hour at 45° C. The reaction products were then separated by centrifugation and counted.

The forward assay was also with 200 λ positive and negative samples. The first incubation sample plus immobilized antibody at 2 levels was for ½ hour at 45° C. This was followed by a wash with Phosphate Buffered Saline, pH 7.4 and then a second incubation with the labeled antibody at 2 count levels for ½ hour at 45° C. The final solid phase products were then washed, separated, and counted.

In yet a further experiment, a "simultaneous" HAA assay was performed by simply incubating the 200 λ positive and negative samples with the tagged antiserum (2 count levels) and the IMAB for one hour at 45° C. The final solid phase products were then washed, separated, and counted for radioactivity as in the forward and reverse assays above. The comparative results are summarized in Table II.

TABLE II

| Reverse Assay | | | |
|---|---|---|---|
| Total Count | Negative | Positive | Amt. of IMAB* |
| 37,000 | 438, 479 | 3573, 3461 | 4X |
| 151,000 | 1308, 1355 | 14,213, 13,707 | 4X |
| 151,000 | 386, 414 | 9386, 9430 | 1X |
| Forward Assay | | | |
| Total Count | Negative | Positive | Amt. of IMAB |
| 37,000 | 223, 150 | 2100, 2050 | 1X |
| 151,000 | 658, 654 | 8754, 8545 | 1X |
| 151,000 | 1509, 1607 | 4620, 4603 | 4X |
| Simultaneous Assay | | | |
| Total Count | Negative | Positive | Amt. of IMAB |
| 37,000 | 558, 580 | 2685, 2642 | 4X |
| 151,000 | 1463, 1647 | 9339, 9007 | 4X |

X = amount of IMAB used in forward or standard sandwich assay.

The above results demonstrate the increased sensitivity obtained using the reverse method.

EXAMPLE III (CEA Assay)

Similar radioimmunoassays were performed to determine concentrations of carcinoembryonic antigen (CEA). For sensitivity comparison purposes, several immunoassays for varying concentrations of CEA were performed in the typical forward mode. For these assays, as well as the reverse assays, the immobilized antibodies comprised composites of anti-CEA antiserum (horse) bonded to 1-3 micron glass particles. The CEA controls were a crude human extract prepared in calf serum. The horse anti-CEA antiserum was labeled with $I^{125}$ using known methods.

To each of 12 plastic test tubes was added 100 λ of a slurry of the immobilized antiserum in phosphate buffered saline (PBS), pH 7.4, containing 0.1% bovine serum albumin (BSA). The tubes were numbered 1-12.

To tubes #1 and #2, 200 λ of "negative" calf serum was added.

To the remaining numbered tubes were added 200 λ samples of varying concentrations of CEA control as follows:

TABLE III

| Tube Nos. | CEA Conc. (ng/ml) |
|---|---|
| 1, 2 | 0 |
| 3, 4 | 0.5 |
| 5, 6 | 2.5 |
| 7, 8 | 12.5 |
| 9, 10 | 50 |
| 11, 12 | 250 |

Each of the tubes was then vortexed and incubated one hour at 45° C. Then, 200λ portions of the $I^{125}$ labeled anti-CEA (100,000 cpm) were added to each tube and the tubes were vortexed and incubated for 3 hours at 45° C. After the incubation period, 3 mls of the buffer were added and the tubes were centrifuged and aspirated. The washing, centrifugation, and aspiration steps were repeated one time and the separated solid phase products were counted for radioactivity with the following results.

TABLE IV

| | (Forward Assay Results) | |
|---|---|---|
| Tube Nos. | CEA Level* (ng/ml) | CPM |
| 1, 2 | 0 | 1882, 1969 |
| 3, 4 | 0.5 | 2188, 2122 |
| 5, 6 | 2.5 | 2218, 2242 |
| 7, 8 | 12.5 | 2462, 2572 |
| 9, 10 | 50 | 8546, 8060 |
| 11, 12 | 250 | 21,598, 21,232 |

*Estimated purity of $I^{125}$ anti-CEA was 30%

The assays were repeated using standards having concentrations indicated below in the reverse mode as follows: 200 lambda portions of the $I^{125}$ anti-CEA (133,000 cpm) and 200 lambda sample size were incubated for 90 minutes at 45° C. The resulting complex was incubated with immobilized anti-CEA for ½ hour at 45° C.

The solid phase products were separated and counted with the following results.

TABLE V

| Tube Nos. | (Reverse Assay Results) CEA Level (ng/ml) | CPM |
|---|---|---|
| 1, 2 | 0 | 3263, 3063 |
| 3, 4 | 1.5 | 3337, 3419 |
| 5, 6 | 7.5 | 4517, 4366 |
| 7, 8 | 15.0 | 5396, 5583 |
| 9, 10 | 30 | 8683, 8334 |
| 11, 12 | 60 | 14,085, 14,176 |
| 13, 14 | 120 | 24,945, 24,474 |

From the above results, the greater sensitivity or signal to noise response obtained using the reverse method of immunoassay is clearly apparent.

It should be understood that the above examples are merely illustrative of the invention disclosed herein. Hence, given this disclosure, it is anticipated that numerous variations will occur to those skilled in the art. Accordingly, it is intended that the spirit and scope of the invention disclosed herein should be limited only by the following claims.

We claim:

1. A method of determining the presence or concentration of a polyvalent antigenic substance in a fluid sample which comprises the steps of:
   (a) incubating the fluid sample with labeled antibodies to the substance under conditions sufficient to form a first labeled immunochemical complex;
   (b) incubating that complex with a composite comprising antibodies to the substance immobilized on a water insoluble carrier material, the incubation being under conditions sufficient to form a second labeled complex comprising the first complex complexed to the composite;
   (c) separating the second labeled complex from the incubation medium;
   (d) determining the amount of label associated with the second complex;
   (e) relating the determination of step (d) to a standard to determine the presence or concentration of the substance in the fluid.

2. The method of claim 1 wherein the labeled antibodies of step (a) are labeled with an enzyme.

3. The method of claim 1 wherein the labeled antibodies of step (a) are labeled with a fluorogenic material.

4. The method of claim 1 wherein the labeled antibodies of step (a) are labeled with a radioisotope.

5. The method of claim 1 wherein the composite of step (b) comprises antibodies immobilized on an organic carrier.

6. The method of claim 1 wherein the composite of step (b) comprises antibodies immobilized on an inorganic carrier.

7. The method of claim 6 wherein the carrier comprises glass particles.

8. The method of claim 1 wherein the determination of step (d) is done enzymatically.

9. The method of claim 1 wherein the determination of step (d) is done fluorometrically.

10. The method of claim 1 wherein the determination of step (d) is done radiometrically.

11. A method of determining the concentration of thyroid stimulating hormone in a human body fluid, the method comprising the steps of:
   (a) incubating the fluid with labeled antibodies to thyroid stimulating hormone under conditions sufficient to complex substantially all of the hormone in the fluid with the antibodies;
   (b) incubating the complexes of step (a) with a composite comprising antibodies to the hormone attached to a water insoluble carrier material, the incubation being under conditions sufficient to assure complexation of substantially all of the labeled complex of step (a) with the composite;
   (c) separating the incubation products of step (b) from the incubation medium;
   (d) determining the amount of label associated with the separated products; and
   (e) relating that determination to a standard to determine the concentration of the thyroid stimulating hormone.

12. The method of claim 11 wherein the labeled antibodies of step (a) are labeled with an enzyme.

13. The method of claim 11 wherein the labeled antibodies of step (a) are labeled with a fluorogenic material.

14. The method of claim 11 wherein the labeled antibodies of step (a) are labeled with a radioisotope.

15. The method of claim 11 wherein the composite of step (b) comprises antibodies immobilized on an organic carrier.

16. The method of claim 11 wherein the composite of step (b) comprises antibodies immobilized on an inorganic carrier.

17. The method of claim 16 wherein the carrier comprises glass particles.

18. A method of detecting the presence of hepatitis associated antigen in a human body fluid, the method comprising the steps of:
   (a) incubating the fluid with labeled antibodies to the antigen, the incubation being under conditions sufficient to complex any antigen in the fluid with the labeled antibodies;
   (b) incubating the complex of step (a) with a composite comprising antibodies to the antigen immobilized on a water insoluble carrier material, the incubation being under conditions sufficient to complex at least a portion of the complex of step (a) with the composite;
   (c) separating the incubation products of step (b) from the incubation medium;
   (d) determining the amount of label associated with the separated incubation products; and
   (e) relating the determination of step (d) to a standard to determine if the antigen is present in the sample.

19. The method of claim 18 wherein the labeled antibodies of step (a) are labeled with an enzyme.

20. The method of claim 18 wherein the labeled antibodies of step (a) are labeled with a fluorogenic material.

21. The method of claim 18 wherein the labeled antibodies of step (a) are labeled with a radioisotope.

22. The method of claim 18 wherein the composite of step (b) comprises antibodies to hepatitis associated antigen immobilized on an organic carrier.

23. The method of claim 18 wherein the composite of step (b) comprises antibodies to hepatitis associated antigens immobilized on an inorganic carrier.

24. The method of claim 23 wherein the inorganic carrier comprises glass particles.

25. A method of determining the concentration of carcinoembryonic antigen in a body fluid, the method comprising the steps of:
(a) incubating the fluid with labeled antibodies to carcinoembryonic antigen under conditions sufficient to complex the antigen with the antibodies;
(b) incubating the complexed products of step (a) with a composite comprising antibodies to carcinoembryonic antigen immobilized on a water insoluble carrier material, the incubation being under conditions sufficient to assure complexation of the complex of step (a) with the composite;
(c) separating the incubation products of step (b) from the incubation medium;
(d) determining the amount of label associated with the separated products; and
(e) relating the determination of step (d) to a standard to determine the concentration of the antigen.

26. The method of claim 25 wherein the labeled antibodies of step (a) are labeled with an enzyme.

27. The method of claim 25 wherein the labeled antibodies of step (a) are labeled with a fluorogenic material.

28. The method of claim 25 wherein the labeled antibodies of step (a) are labeled with a radioisotope.

29. The method of claim 25 wherein the composite of step (b) comprises antibodies to the antigen immobilized on an organic carrier.

30. The method of claim 25 wherein the composite of step (b) comprises antibodies to the antigen immobilized on an inorganic carrier.

31. The method of claim 30 wherein the carrier comprises glass particles.

* * * * *

UNITED STATES PATENT OFFICE
CERTIFICATE OF CORRECTION

PATENT NO. : 4,098,876
DATED : July 4, 1978
INVENTOR(S) : Roger N. Piasio, James W. Ryan, James E. Woiszwillo It is certified that error appears in the above-identified patent and that said Letters Patent are hereby corrected as shown below:

Column 1, line 57, "insloluble" should be -- insoluble --.

Column 3, lines 20-21, "mechanisms" should be -- mechanism --.

Column 3, line 64, "ample" should be -- sample --.

Column 4, line 35, "AB* + AG → AB*.Ag" should be
-- Ab* + Ag → Ab*.Ag --.

Column 4, line 68 and column 5, line 1, "AB*.AG + IMAB → AB*.Ag.IMAB," should be -- Ab*.Ag + IMAB → Ab*.Ag.IMAB, --.

Column 5, line 5, "(AB*.Ag-" should be -- (Ab*.Ag- --.

Column 5, line 24, "(AB*" should be -- (Ab* --.

Column 5, line 49, "exaple," should be -- example --.

Signed and Sealed this

Twenty-fourth Day of April 1979

[SEAL]

Attest:

RUTH C. MASON
Attesting Officer

DONALD W. BANNER
Commissioner of Patents and Trademarks